(12) United States Patent
Neusidl et al.

(10) Patent No.: US 8,206,441 B2
(45) Date of Patent: Jun. 26, 2012

(54) CORNEAL ENDOTHELIAL TISSUE INSERTER

(75) Inventors: William B. Neusidl, Phillipsburg, NJ (US); Craig L. Fischer, Imperial, MO (US); Greg Gordon Utt, Warrenton, MO (US)

(73) Assignee: Fischer Surgical, Inc., Imperial, MO (US)

( * ) Notice: Subject to any disclaimer, the term of this patent is extended or adjusted under 35 U.S.C. 154(b) by 32 days.

(21) Appl. No.: 12/833,794

(22) Filed: Jul. 9, 2010

(65) Prior Publication Data

US 2010/0274257 A1  Oct. 28, 2010

Related U.S. Application Data

(63) Continuation-in-part of application No. 12/027,822, filed on Feb. 7, 2008, now abandoned.

(60) Provisional application No. 60/889,236, filed on Feb. 9, 2007.

(51) Int. Cl.
*A61F 2/16* (2006.01)

(52) U.S. Cl. ........................................ 623/6.12

(58) Field of Classification Search .................. 623/6.12; 606/107, 166, 184, 185; 604/22, 27
See application file for complete search history.

(56) References Cited

U.S. PATENT DOCUMENTS

| | | | | |
|---|---|---|---|---|
| 4,699,140 | A * | 10/1987 | Holmes et al. | 606/107 |
| 5,772,667 | A * | 6/1998 | Blake | 606/107 |
| 5,776,112 | A * | 7/1998 | Stephens et al. | 604/264 |
| 2008/0161845 | A1 * | 7/2008 | Murakami et al. | 606/185 |

* cited by examiner

*Primary Examiner* — S. Thomas Hughes
*Assistant Examiner* — Katherine M Shi
(74) *Attorney, Agent, or Firm* — Charles McCloskey

(57) ABSTRACT

A device transfers donor endothelial cells to the cornea of a recipient without injuring the cells or the cornea during the transfer process. The device transfers living endothelial cells from a donor to a recipient with minimal or no trauma. The device includes a handle, an irrigation tube lengthwise within the handle, a button upon the handle concentric with the irrigation tube, a tapered nose opposite the button, a forward tube extending outwardly from the nose, and a platform joined to the irrigation tube. The forward tube has an elliptical cross section and two beveled features. The platform has two wings that curl gently around donor tissue upon retracting the platform into the forward tube. The handle has a groove for a stem of a knob that surgeon presses and pulls to move the platform.

8 Claims, 12 Drawing Sheets

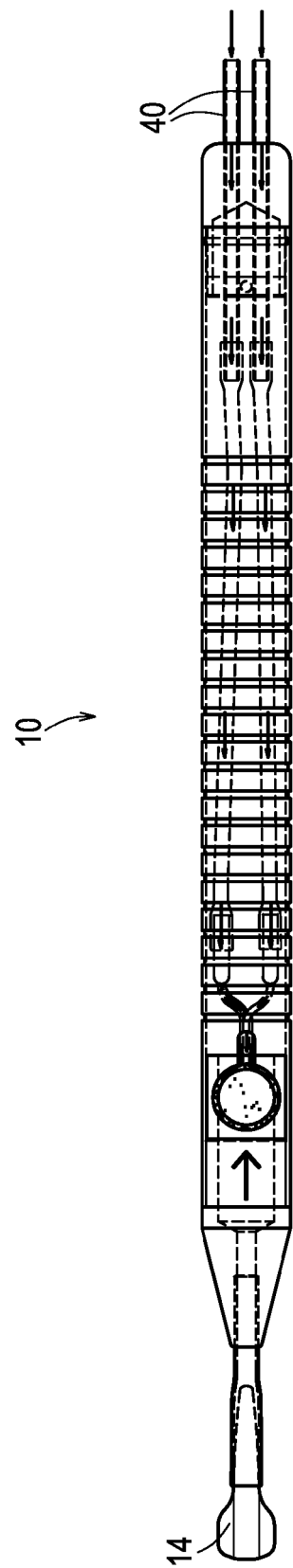

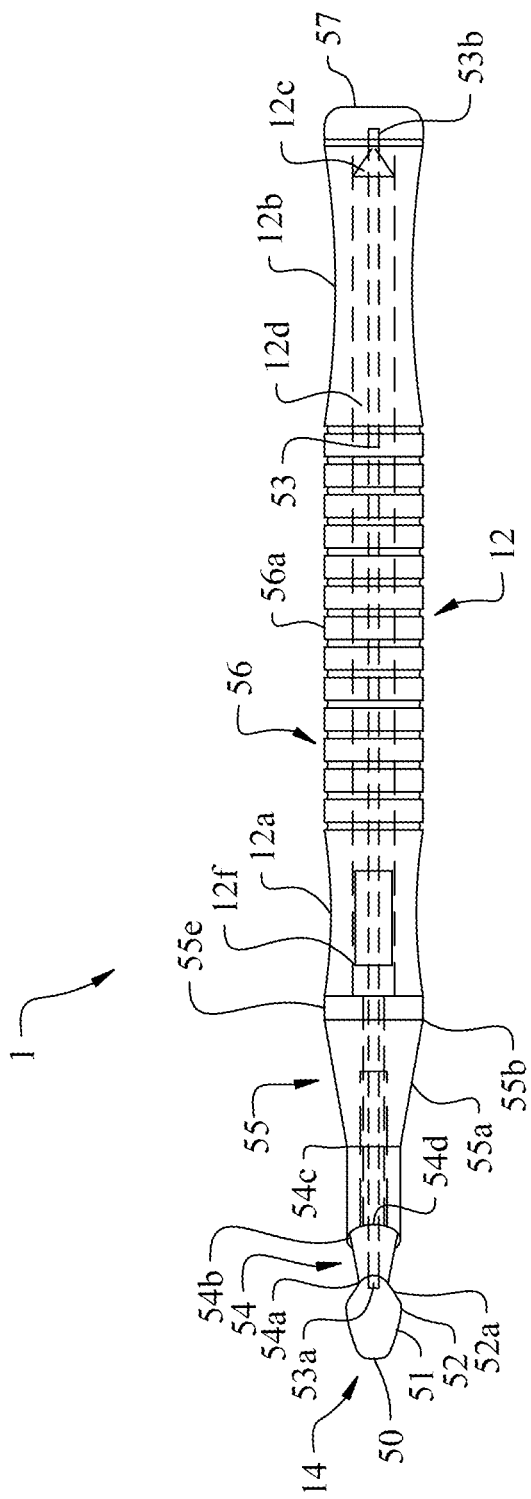
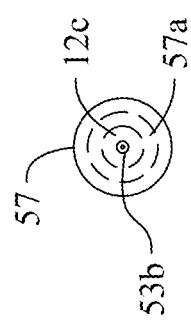
Fig. 8
Fig. 8a

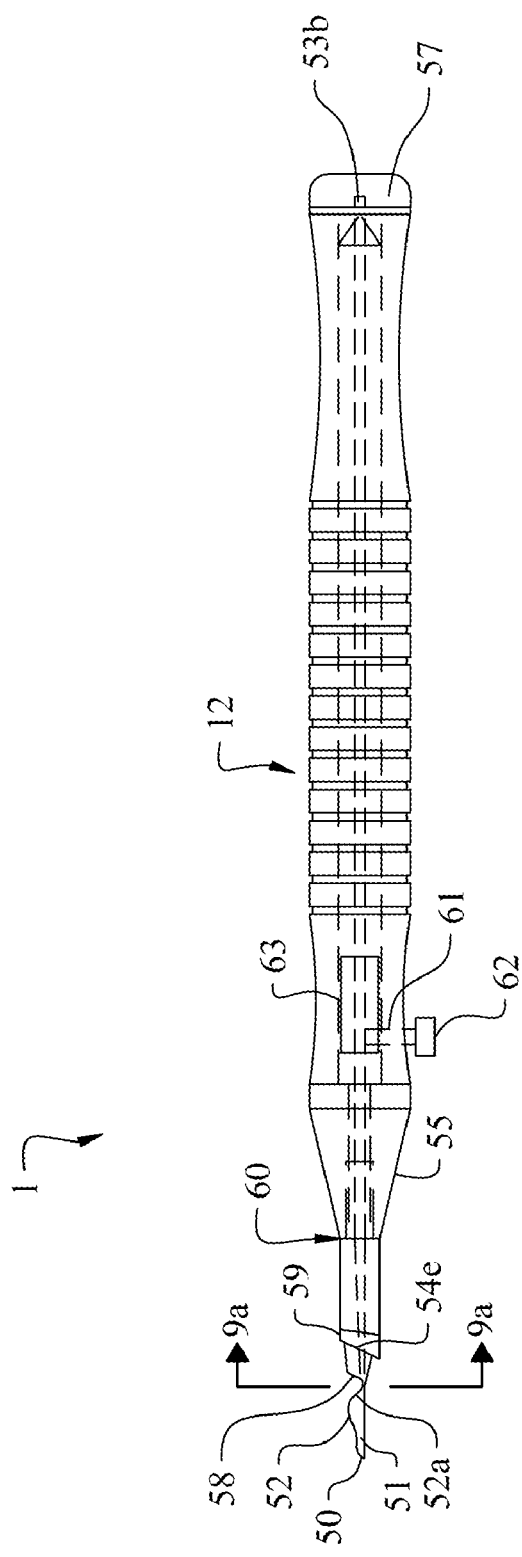
Fig. 9
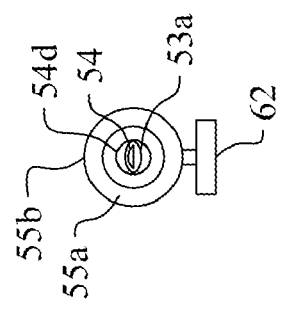
Fig. 9a
Fig. 9b

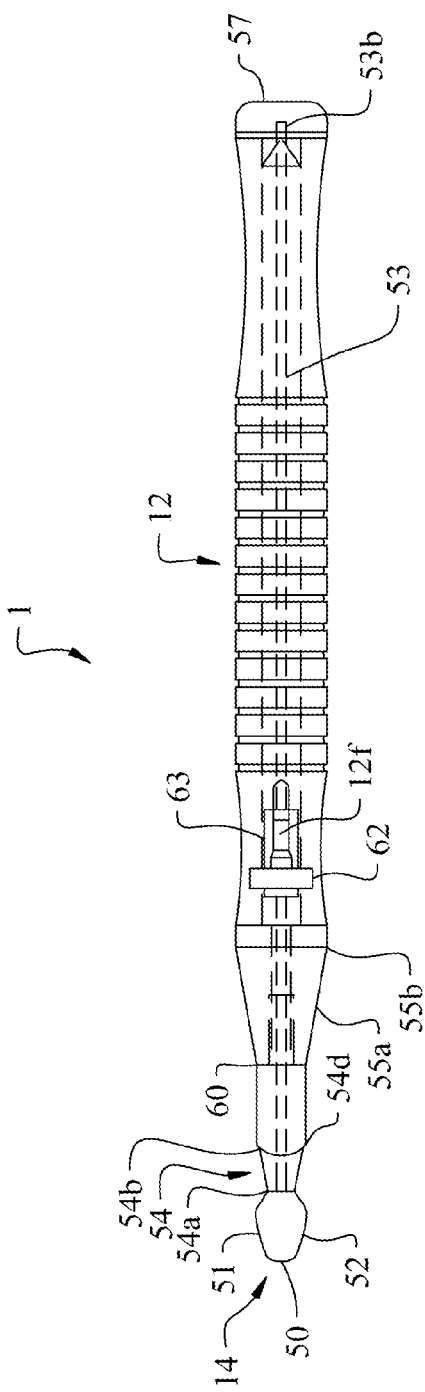
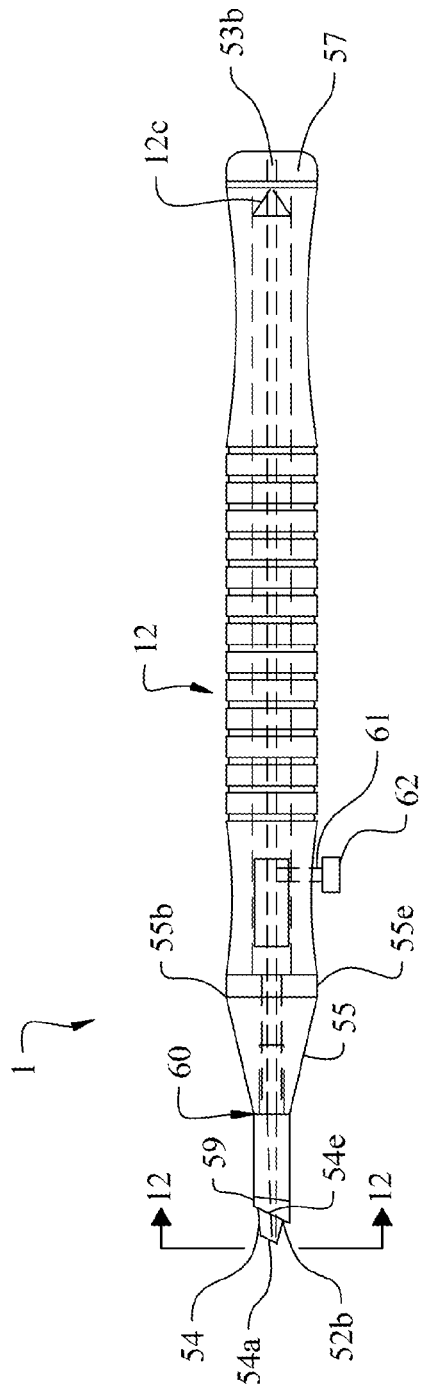
Fig. 10
Fig. 11

CORNEAL ENDOTHELIAL TISSUE INSERTER

CROSS-REFERENCE TO RELATED APPLICATION

This non-provisional application is a continuation in part of the non-provisional application for patent having the U.S. Ser. No. 12/027,822 filed on Feb. 7, 2008 now abandoned which claims priority to the expired provisional application having the U.S. Ser. No. 60/889,236 filed on Feb. 9, 2007 and both are owned by the same assignee, and both disclosures are incorporated by reference.

BACKGROUND OF THE INVENTION

The corneal endothelial tissue inserter relates to medical devices that work with eye tissue and more specifically to a device that retracts an extremely thin layer of donor endothelial eye tissue and then places this tissue within the eye of a recipient.

People have eyes to see. An eye has various parts that receive and focus light upon a retina that converts the light into electrical signals transmitted to a is person's brain for interpretation. In the vicinity of a person, light encounters a cornea as the first part of the eye. The cornea, generally transparent, admits light further into the eye. The cornea has its own constituent parts where the endothelium is the extremely thin, innermost layer of the cornea. Endothelial cells serve an essential purpose to keep the cornea clear, that is, transparent. Normally, fluid, vitreous humor, leaks slowly from inside the eye into the middle corneal layer, or stroma. The endothelium's primary task involves pumping this excess fluid, now aqueous humor, out of the stroma. Without this pumping action, the stroma swells with water, becomes hazy and ultimately opaque leading progressively to blindness. A healthy eye has a perfect balance between the fluid moving into the cornea and fluid being pumped out of the cornea. Upon destruction of endothelium cells by disease or trauma, those cells become lost forever. With too many endothelial cells destroyed, corneal edema and blindness ensue requiring the only therapy, corneal transplantation.

Over the years, various physicians and instrument manufacturers have attempted to collect, to maintain, to remove, and to transplant endothelial cells from a donor eye to a recipient. Physicians have developed the technique of Descemet's stripping with endothelial keratoplasty (DSEK) to repair afflicted corneas. Few, if any instruments and techniques allow for ready transplant of endothelial cells. A precursor technique incises a donor cornea upwardly of five mm and retrieves endothelial cells using an ophthalmic forceps. Upon removing the cells from the donor and then inserting the cells through a five mm opening in a recipient's eye, the forceps far too often crush and damage the endothelial cells and select adjacent tissue in the recipient's eye.

DESCRIPTION OF THE PRIOR ART

However, instrument makers and physicians continue to seek better ways is of transplanting endothelial cells. Various instrument patents have appeared over the years. The U.S. Pat. No. 5,098,439 to Hill et al. describes an apparatus that inserts lenses intraocular. The apparatus has a foldable paddle upon a mechanism within a tube. The paddle carries a foldable lens through an incision in an eye. However, the tube 214 has a generally constant outer diameter, a round shape, and a square end as in FIG. 6 of Hill.

The U.S. Pat. No. 5,876,440 to Feingold illustrates a method to use a device implanting an intraocular lens in an eye. The device utilizes a knob 18 upon a threaded cylinder within a threaded handle. Turning of the knob advance the threaded cylinder into the handle thus moving a cartridge forwardly so a tip 20 may insert a lens. However, the tip does not enwrap tissue and the tip surfaces taper inwardly, opposite of the present invention.

And Van Gent has U.S. Pat. No. 4,955,889 for an eye lens insertion apparatus. This apparatus utilizes a heating system that extends into a cradle. The cradle has a shape memory material that unfolds upon reaching a select temperature. This apparatus though lacks an irrigation system and folding of the cradle without an overlap.

The present invention overcomes the disadvantages of the prior art and provides a paddle that rolls endothelial tissue upon it without folding, produces 30% less tissue damage than existing techniques, provides proper orientation of the tissue in the recipient's eye, prevents physicians from inserting the tip too far into the eye, and treats adult, pediatric, and Asiatic eye types. The instrument of the present invention allows for the transfer of living endothelial cells with minimal or no trauma.

SUMMARY OF THE INVENTION

Generally, the corneal endothelial tissue inserter has a reusable, hollow rigid tube, or barrel, that has a disposable tissue holder, or transfer chamber, at its distal end. This holder is generally a soft, plastic platform-paddle connected to the barrel by a thin rod, or tube, advanced from or retracted into the barrel by turning a knob at the proximal end. The tube allows for irrigation of the paddle and tissue thereon during usage of the invention. The knob operates upon a threaded system and advances or retracts the paddle at multiple positions while a surgeon holds the instrument. The platform also advances or retracts by sliding a flow regulator ring forward or backward. The flow regulator ring connects to the rod with a lumen. The lumen connects to the disposable platform that houses and protects the donated endothelial tissue during the transfer process.

Turning the knob retracts the paddle into the barrel and causes the soft plastic paddle to conform to the walls of the barrel, thus folding the paddle into a cylinder slightly smaller in diameter than the internal diameter of the distal end of the tapered barrel opening. This operation gently rolls the corneal endothelial tissue seated on the inside of the paddle with no acute folds. Depending on the diameter of the paddle, a surgeon may roll the tissue using the bi-fold, that is 60/40, or tri-fold, or taco, techniques. Because the tissue transfers from the donor eye without forceps and no forcing of the tissue through a small incision occurs, these rolling techniques have relatively safe use. The paddle rolls the tissue within the elliptical tube and protects the vital cells during the transfer process through a small incision. The paddle, made of a flexible soft plastic, can have different diameters that ease transplantation through different size incisions. Rolling the tissue allows for a transfer device that use a smaller paddle and thus smaller incisions in the donor and recipient eyes. The soft material of the paddle surrounds the tissue and protects it during the transfer process, that is, no crushing and no squeezing through an incision as in the prior art forceps transfer. After retracting the paddle that houses and protects the tissue, the surgeon inserts the distal, tapered end of the barrel into the incision in the recipient's eye. The physician receives a tactile indication to halt the insertion from a tapered stop that abuts the surface of the eye. Rotating the knob to extend the rod causes the paddle to unroll thereby allowing the tissue to release and naturally resume its shape. Irrigation, controlled with a flow regulator, upon demand supplies lubrication if the tissue sticks to the paddle or resists unrolling or if the anterior chamber requires support during transfer.

Further, different size platforms may see use to house the tissue during the tissue transfer process. Other devices for retracting the platform within the protective barrel remain available such as threads or push rod.

There has thus been outlined, rather broadly, the more important features of the invention in order that the detailed description thereof that follows may be better understood and that the present contribution to the art may be better appreciated. Additional features of the invention will be described hereinafter and which will form the subject matter of the claims attached.

Numerous objects, features and advantages of the present invention will be readily apparent to those of ordinary skill in the art upon a reading of the following detailed description of the presently preferred, but nonetheless illustrative, embodiment of the present invention when taken in conjunction with the accompanying drawings. Before explaining the current embodiment of the invention in detail, it is to be understood that the invention is not limited in its application to the details of construction and to the arrangements of the components set forth in the following description or illustrated in the drawings. The invention is capable of other embodiments and of being practiced and is carried out in various ways. Also, the phraseology and terminology employed herein are for the purpose of description and should not be regarded as limiting.

One object of the corneal endothelial tissue inserter is to provide an inserter that can readily collect, transport, and deliver endothelial tissue without folding.

Another object of the corneal endothelial tissue inserter is to provide such an inserter that produces less cell damage than existing devices.

Another object of the corneal endothelial tissue inserter is to provide such an inserter that readily provides complete control of the device by the surgeon before, during, and after usage.

Another object of the corneal endothelial tissue inserter is to provide such an inserter that has a tip arrangement that limits further insertion of the tip by the surgeon.

Another object of the corneal endothelial tissue inserter is to provide such an inserter that has a tip arrangement that avoids inadvertent adherence to eye tissue during usage.

Another object of the corneal endothelial tissue inserter is to provide such an inserter that has a low cost of manufacturing so the surgeons and hospitals can readily purchase the inserter through existing medical supply outlets.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

In referring to the drawings,

FIG. 7 shows a top view of a second alternate embodiment of the instrument;

FIG. 8 shows a top view of the preferred embodiment of the instrument when presenting tissue;

FIG. 8a describes a rear view of the preferred embodiment of the instrument;

FIG. 9 illustrates a side view of the instrument;

FIG. 9a shows a front view of the instrument;

FIG. 9b shows a front view of the instrument;

FIG. 10 provides a bottom view of the instrument;

FIG. 11 shows a top view of the preferred embodiment of the instrument but with the platform retracted;

The same reference numerals refer to the same parts throughout the various figures.

DESCRIPTION OF THE PREFERRED EMBODIMENT

Figure 1:
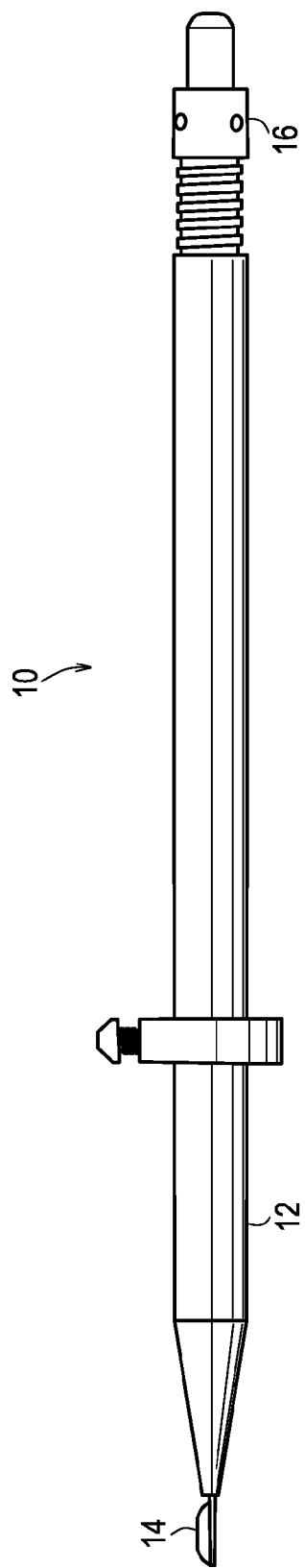
FIG. 1 illustrates a side view of an instrument, in accordance with an embodiment of the present invention.
Figure 2:
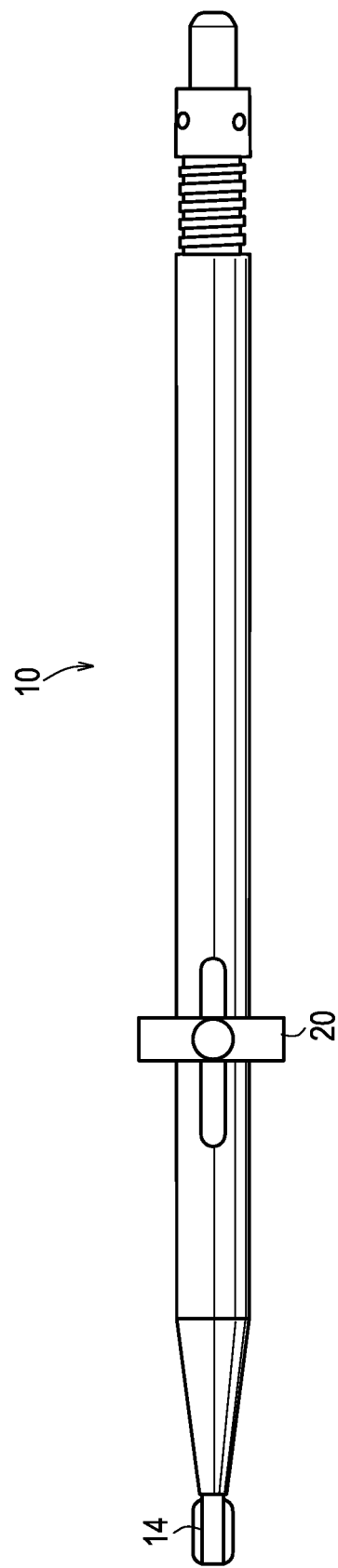
FIG. 2 describes a top view of an embodiment of the instrument.
Figure 3:
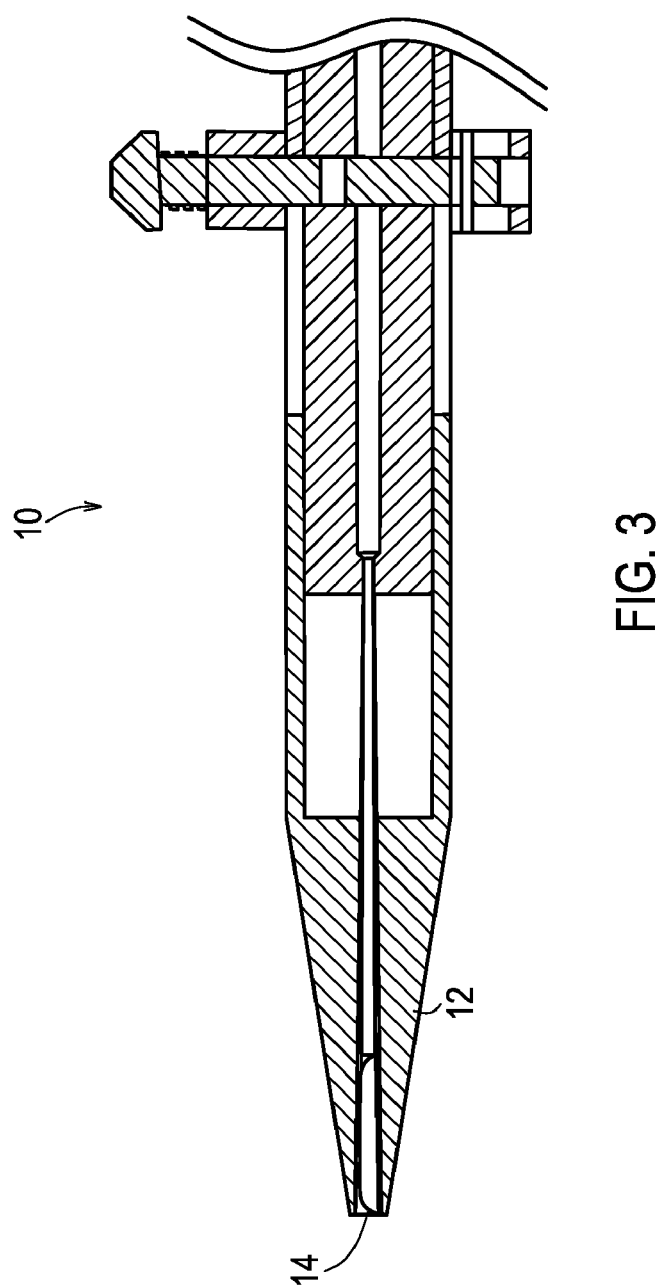
FIG. 3 shows a partial cross section of the opposite of distal end of the instrument.

The present invention overcomes the prior art limitations by providing an instrument that retrieves and delivers endothelial tissue without damage to the tissue and recipient eye. Referring now to FIG. 1, it shows an alternate embodiment in a side view of an instrument 10. This instrument has a hollow rigid tube, like a barrel or handle 12 with a disposable tissue holder or transfer chamber 14 at a distal end of the instrument. The holder 14, or platform, advances forward or retracts rearward into the barrel 12 by pushing or pulling a tab 16 at a proximal end of the barrel 12. Referring to FIG. 2, it shows an alternate embodiment in a top view of the instrument 10. The instrument also includes a flow regulator ring 20 that also moves forward or rearward to advance or retract the tissue holder or platform 14. Next, FIG. 3 shows a side sectional view of the alternate embodiment of instrument 10 with the holder 14 retracted completely into barrel 12.

Figure 4:
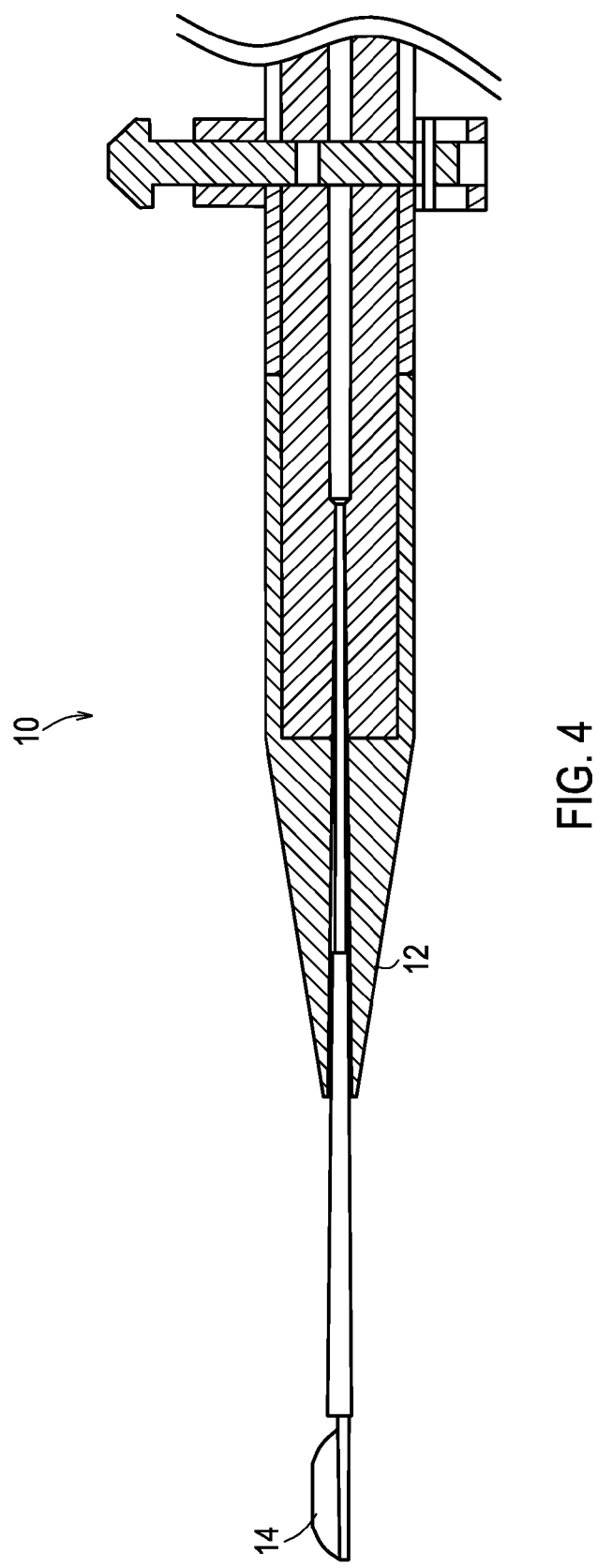
FIG. 4 shows the partial cross section of FIG. 3 where the paddle is extended outwardly from the instrument.
Figure 5B:
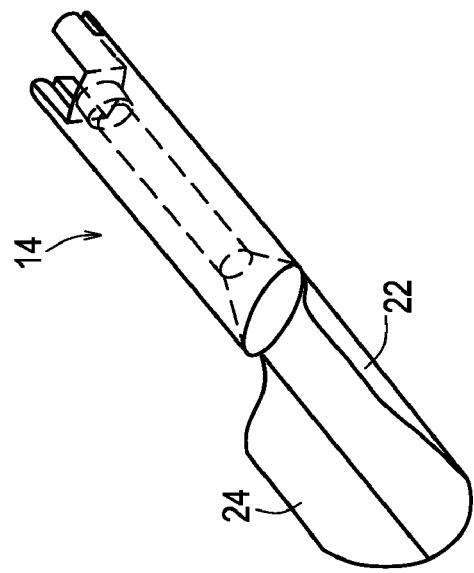
FIG. 5b illustrates a detailed view of a paddle having long outward wings.
Figure 5A:
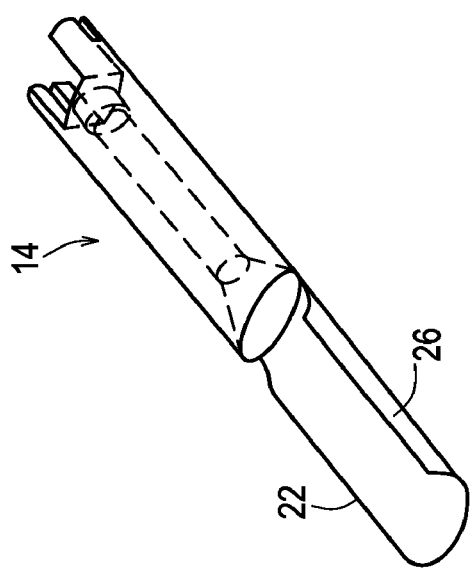
FIG. 5a illustrates a detailed view of a paddle having short outward wings.
Figure 6C:
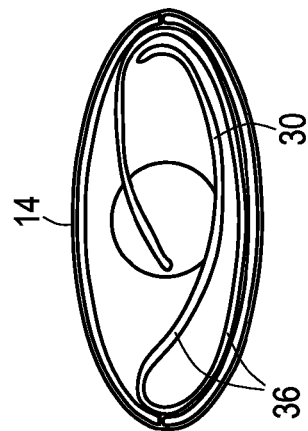
FIG. 6c describes an end view of a paddle retracted with a right wing flexing above a left wing.
Figure 6B:
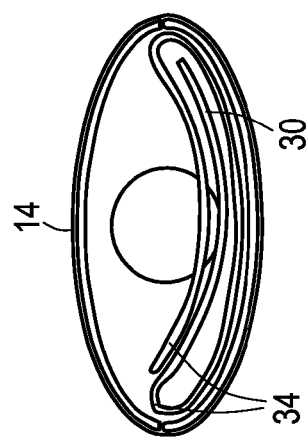
FIG. 6b describes an end view of a paddle retracted but with a right wing overlapping a left wing.
Figure 6A:
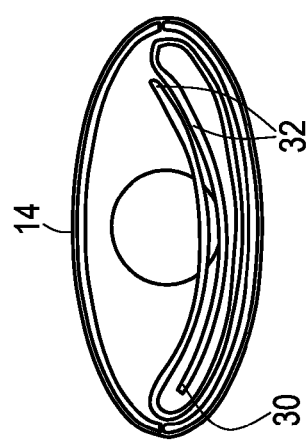
FIG. 6a describes an end view of a paddle retracted with a left wing overlapping a right wing.

Turning to FIG. 4, the alternate embodiment of the instrument appears in a side view with the holder 14 advanced fully forward of the barrel 12. Referring to FIGS. 5a and 5b, alternate embodiments shown have a tissue holder 14 that is retracts and advances and has tissue holder flaps 22 that attain a platform open position 24 and platform closed position 26. The tissue holder flaps 22 conform to the walls of the barrel 12 and form a cylindrical shape to insert easily into the barrel 12. Then referring to FIGS. 6a, 6b, 6c, the instrument appears in an end view with the platform forward. More particularly, FIG. 6a shows the initial folding of the flaps 22 around corneal endothelial tissue 30 into a trifold arrangement as at 32. FIG. 6b provides an illustration of folding the flaps 22 around the corneal endothelial tissue 30 into a reverse trifold arrangement as at 34. Then FIG. 6c describes folding of the flaps 22 around the corneal endothelial tissue 30 in a bifold arrangement as at 36.

Referring to FIG. 7, an alternate embodiment of the present invention appears in a top view of the instrument 10. This alternate embodiment has two irrigation channels 40 that provide fluids to the platform 14, if the tissue 30 sticks to the platform 14 or the tissue 30 resists unfolding once the platform 14 is open. The fluid from the irrigation channels also maintains the anterior chamber of the eye during the transfer of tissue 30 into the eye.

Then FIG. 8 shows the preferred embodiment of the instrument 10 from the top as seen by a surgeon during usage. The instrument has a length, a width perpendicular to the length, and a longitudinal axis generally centered upon the length. The instrument has its platform 14 show fully extended outwardly. The platform has a blunted spade like shape with a leading edge 50 substantially perpendicular to the longitudinal axis. The leading edge has a generally convex shape with a radius of curvature greater than the width of the platform. The leading edge has two ends that each begin a wing 51. Each wing extends outwardly from the longitudinal axis and rearwardly from the leading edge 50. Each wing widens rearwardly from the leading edge until each wing reaches an inflection point 52 which denotes the maximum width of the platform. Rearwardly is of the inflection points, the platform sharply narrows in width along its trailing edges 52a. The platform joins to an irrigation tube 53 at the forward end 53a of the irrigation tube.

The irrigation tube is hollow, slender, and elongated with a length slightly less than the entire length of the instrument. Opposite the forward end 53a, the irrigation tube has its rear end 53b. As shown in this figure, the forward end 53a extends slightly outwardly from the remainder of the instrument while the rear end 53b remains interiorly from the remainder of the instrument.

Rearward of the platform 14 and the forward end 53a, the instrument has its forward tube 54 of lesser width than the leading edge 50 of the platform. The forward tube begins at a narrow width, as at 54a, that widens away from the platform to its maximum width, as at 54b. The forward tube is generally hollow and has an elliptical cross section as later shown in FIG. 9a. The elliptical cross section extends from the narrow width, as at 54a, of the tube rearward to the maximum width, as at 54b. Rearward of the maximum width, as at 54b, the forward tube has an increase in thickness around its perimeter for the remainder of its length away from the platform. The increase in thickness begins along a bevel from the side of the instrument. In this figure, the bevel appears as a partial arc, as at 54d, having a radius of curvature exceeding the widest width of the forward tube.

Opposite the narrow width, as at 54a, of the forward tube, the instrument continues with a nose 55 joined to a far end 54c of the forward tube. The nose begins with a greater diameter than the far end 54c that expands to a maximum diameter for short length as at 55b. The nose serves as the truncated apex of a round cone while the nose has a hollow frusto-conical shape beginning just behind the far end and expanding in diameter to its maximum at 55b. The nose has a length from smaller to larger diameter, as at 55a. Rearward, that is, away is from the platform, the nose has a short length, as at 55c, at its maximum diameter. Then rearward from the nose, the instrument has its handle 12 at a diameter slightly larger than the maximum diameter of the nose.

Like the forward tube and the nose, the handle remains hollow and coaxial with the nose and the forward tube. Somewhat near the platform, the handle has its proximal grip 12a with a generally slight concave shape suitable for griping by the thumb and forefinger of a surgeon. The proximal grip extends around the entire perimeter of the handle to allow a surgeon to rotate the instrument while maintaining a grasp of it. The proximate grip has a radius of curvature generally greater than the length of the instrument. Rearwardly from the proximal grip, the handle has a section of ribbing 56 formed of a plurality of ribs, 56a. Each rib has a maximum diameter that of the maximal diameter of the proximal grip, that is, the diameter of the handle. Between adjacent ribs, a gap has a slightly lesser diameter than the ribs that provides a grasping surface of the palm of the surgeon's hand. The ribbing extends for at least one quarter of the overall length of the instrument. Rearwardly from the ribbing, the handle has its distal grip 12b. The distal grip also has a generally slight concave shape suitable for griping by the palm and little finger of a surgeon. The distal grip also extends around the entire perimeter of the handle to allow a surgeon to rotate the instrument while maintaining a grasp of it. The distal grip has a length along the instrument generally greater than the proximate grip. The distal grip has a radius of curvature generally greater than the length of the instrument. The distal grip begins and ends at the diameter of the instrument. And rearwardly from the distal grip, that is, distally upon the instrument, the handle has its button 57 generally a short cylinder, round in shape, with a rounded edge. The button rotates about an axis coaxial with the longitudinal axis of the instrument. The button has a socket 57a for receiving an irrigation supply line, not shown, that is connects to the irrigation tube 53.

The irrigation tube, shown in phantom, extends for the length of the instrument 1. The irrigation tube has its forward end 53a that connects with the platform 14 proximate the trailing edges 52a. The tube then passes through the forward tube 54, the nose 55, the handle 12, and has its rear end 53b entering the button socket 57a. Proximate the button socket, the handle has a reinforcing cone 12c centered upon the rear end 53b. The tube extends outwardly from the apex of the cone 12c for a sufficient distance suitable for the tube to connect with a supply line. The reinforcing cone has a maximum diameter inwardly from the button and an opening through the height of the cone for the irrigation tube. The opening has a diameter similar to that of the irrigation tube for its tight fit into the opening.

As described, the irrigation tube extends lengthwise through the handle 12. For passage of the irrigation tube, the handle has a chamber 12d having a diameter greater than that of the irrigation tube and less than the diameter of the button. The chamber's diameter is also less than the narrowest diameter of either the proximal grip or the distal grip. The chamber extends from just inside of the button 57 forwardly through the distal grip, ribbing, and proximal grip. The chamber is generally coaxial with the longitudinal axis of the instrument. Where the straight portion 55e of the nose adjoins the handle as shown, the chamber steps inwardly in diameter, as at 12e, forming an inner diameter through the forward tube in within the nose. Forwardly from the step, the chamber has a lesser diameter than when in the handle. The lesser diameter extends for the length of the nose. The forward tube 53 then fits into the lesser diameter of the chamber proximate the apex of the nose 55.

Viewing the button 57, FIG. 8a shows the instrument 1 from the rear, or as is in the surgeon's hand proximate the little finger during usage. The button is generally round in shape having a diameter similar to that of the handle 12. Generally centered upon the button, the socket 57a is recessed inwardly but not completely through the thickness of the button. The socket has a diameter that receives an irrigation supply line.

The socket diameter generally exceeds that of the irrigation tube. Proximate the interior of the socket, the rear end 53b of the irrigation tube occupies the center of the socket. The rear end 53b enters the socket partially through its depth but does not exit the socket, or extend beyond the button. Outwardly from the rear end and inwardly from the socket, the reinforcing cone 12c appears in an end view of its apex.

Turning the invention, FIG. 9 illustrates the instrument from the side in an orientation for use by a surgeon. This view begins with the platform 14 extended from the handle 12 to the left. The platform has its leading edge 50 to the left and then its wing 51 here shown slightly curved upwardly to its inflection point 52. Rearward of the inflection point, the platform shows its trailing edge 52a. The trailing edges merge as the platform 14 joins to the forward end 53a of the irrigation tube. The platform has a generally flat orientation as it joins the forward end 53a.

Rearward from the platform, the forward tube 54 has a bevel 58 angled away from the platform and towards the handle. The bevel extends across the narrow width 54a of the forward tube. The bevel occupies a plane at less than ninety degrees from the longitudinal axis of the instrument. The bevel 58 and curved arc of the narrow width 54a cooperate to guide the instrument to a proper orientation upon the eyeball of a recipient of endothelial tissue. The narrow width of the forward tube fits into a precise incision in the recipient's eyeball. Away from the bevel, the forward tube grows slightly in its height. Where the forward tube has its maximum width, 54b, it also has its maximum height as at 54e. At its maximum height, the forward tube steps outwardly in thickness as previously described along a second bevel 59. The second bevel is generally parallel to the first bevel 58 though extending slightly higher and slightly lower as shown. The second bevel with slightly larger width and height than the first bevel provides a tactile warning to the surgeon that the instrument has inserted into the recipient's eye for the maximum distance.

In the preferred embodiment, the forward tube extends away from the second bevel at a constant height and width. The forward tube then joins the nose as previously described. In an alternate embodiment, the forward tube has a slight increase in height in this view at its neck 60 proximate the nose.

Within the forward tube, the irrigation tube 53 extends away from the platform 14. Proximate the platform, the irrigation tube has a closed, rounded forward end. Away from the forward end, which is towards the grip of the handle, the irrigation tube has an angled cut to its opening. This angled cut provides for the exit of irrigation fluid and for a connection to the trailing end of the platform. The connection is somewhat hemispherical when viewed on end as in FIG. 9b. Rearward from the connection the irrigation tube returns to its outside diameter for the remainder of its length. Perpendicular to the irrigation tube, a stem 61 extends outwardly from the irrigation tube and also opposite from the curl of the platform 14. The stem extends outwardly from the proximal grip 12 and slightly more than the maximum diameter of the nose as at 55c. The stem has a bar 62 or tab upon its end opposite the irrigation tube. The stem also fits into a slider 63. The slider is preferably a round cylinder within the chamber 12d that has a diameter slightly less than the diameter of the channel. The slider also has the irrigation tube passing through it lengthwise. The stem has a position upon the slider so that when the stem is advance forward towards the nose, the slider abuts the end of the chamber as at 55e preventing further inadvertent insertion is of the platform into a recipient's eye. The slider reinforces the connection between the stem and the tube so that the stem does not bend the tube or otherwise jam the instrument. The slider itself has a length less than the length of the proximal grip of the handle. By pushing and pulling the bar, a surgeon advances and retracts the platform within a defined distance.

Viewing the front of the instrument 1, FIG. 9a shows the platform fully extended outwardly from the plane of the figure. The platform 14 is primarily flat in its center between the wings 51 behind the leading edge 50. The wings curve upwardly, that is, away from the tab 62. Opposite the leading edge 50 the platform joins to the forward end 53 of the irrigation tube. At the forward end, the tube has a generally hemispherical closure providing a solid end that does not allow straight passage of irrigation fluid upon the platform. Away from the forward end, the irrigation tube has an angled cut to its opening and the irrigation fluid exits the irrigation tube from there for a more smooth flow of the irrigation fluid onto the platform.

Similar to FIG. 9a, FIG. 9b shows the platform fully retracted into the forward tube. The forward tube has its elliptical shape of its narrow end 54a. When a surgeon retracts the tab upon the stem and pulls the platform rearwardly, the trailing edges 52a gently curl the wings 51 upwardly and inwardly but not so far that the trailing edges contact each other. The platform 14 along with the tube 53 retract into the handle 12 as the slider 63 retracts under the control of the surgeon.

Then FIG. 10 provides a bottom view of the instrument, that is, the area of the invention gripped by the surgeon during usage. The instrument 1 has its platform 14 here shown fully extended. Behind the leading edge 50, the wings 51 have a slight curl into the plane of the figure. The trailing edges 52 then contact the narrow width, as at 54a, of the forward tube 54. The forward tube is then expands outwardly and rearwardly to its maximum width as at 54b. The curve, 54c, denoting the maximum width is generally opposite that portion shown in FIG. 8. The narrow width and maximum width show the forward tube as having an outwardly expanding cross section. At the curve of maximum width, the forward tube has a stepped increase in height and width, as at 54c, and extends rearwardly at a constant width and height. With the irrigation tube inside of it, the forward tube joins to the nose 55 that expands its conical shape to its maximum diameter as at 55b. The nose then has its small portion of constant diameter 55e that matches with the proximal grip 12a of the handle 12. Generally centered and extending parallel to the longitudinal axis of the handle, the proximal grip includes the slider 63 passing within the chamber 12d. As before the slider has a diameter and length for a snug but moveable fit within the chamber. Outwardly from the slider, the proximal grip includes a slot 12e. The slot has a narrower width than the diameter of the slider 63. The slot defines the forward and rearward limits for the stem beneath the bar 62. The forward limit in cooperation with the stem advances the platform to its fully extended position as shown. Opposite the panel, the irrigation tube 53b extends slightly outwardly from the vicinity of the distal grip.

Similar to FIG. 10, FIG. 11 shows the instrument from the bottom but with the platform 14 fully retracted. The platform curls its wings 51 slightly away from the plane of the figure and within the forward end 53a of the forward tube. The tab 62 retracts the stem and the slider 63 rearwardly. As the slider moves, the tube 53 also moves rearwardly. In doing so, the rear end 53b of the irrigation tube moves outwardly from the reinforcing cone 12, further into the button 57 but not through the button. During movement of the rear end 53b, any supply line remains connected.

Figure 12:
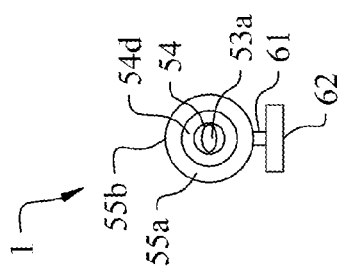
FIG. 12 provides an end view of the instrument with a retracted platform.

Then FIG. 12 describes a front view of the invention with the platform 14 is retracted into the forward tube 54. The forward tube has its narrow width 54a surrounding the platform in this view. The forward tube has a generally elliptical shape. Being elliptical, the cross section of the forward tube has a major axis and a perpendicular minor axis. The major axis is generally perpendicular to the stem while the minor axis is generally parallel to the stem. Rearwardly from the narrow width 54a, the forward tube expands slightly outwardly along the major and minor axes to the bevel 54e. Rearwardly from the bevel, the forward tube has its increase in thickness from its maximum width 54b to its junction with the nose 55 having its length, as at 55a, and its maximum diameter as at 55b.

Figure 13:
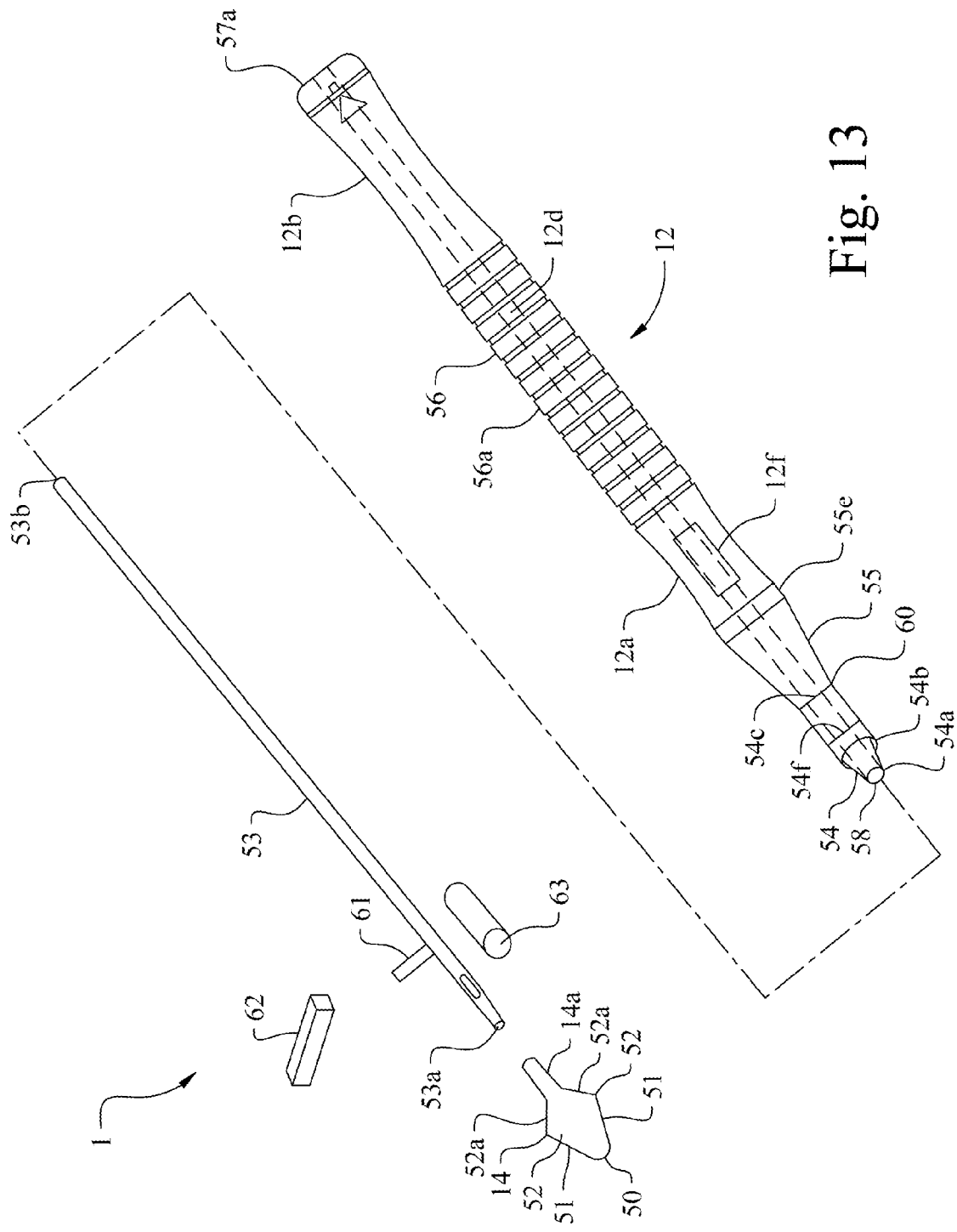
FIG. 13 describes an exploded view of the instrument.

FIG. 13 then illustrates an exploded view of the invention beginning with the platform 14. The platform has a spade like shape with its leading edge 50, wings 51, and trailing edges 52. The trailing edges merges into a tang 14a of narrower width than the leading edge. The tang connects with the forward end 53a of the irrigation tube 53. The irrigation tube is generally hollow, elongated, and slender as previously described. A certain distance inward from the forward end, the stem 61 joins perpendicular to the irrigation tube. The stem and the tang join to the same side of the irrigation tube, that is, the wings of the platform curl opposite the stem. The stem fits into the slider 63 that itself fits into the chamber 12d of the handle 12. Outwardly of the slider and the instrument 1, a tab 62 connects to the end of the stem opposite the irrigation tube. Opposite the forward end 53a, the irrigation tube has its rear end 53b, generally open for connection to a supply line. The handle 12 begins with the narrow width 54a of the forward tube 54. Then the forward tube expands in height and width to its maximum at 54b. The forward tube then steps outwardly its thickness until it joins the nose 55. The nose has its frustoconical shape that expands outwardly to the maximum diameter of the handle, as at 55b. The handle 12 then has its proximal grip 12a with the groove 12f for the stem. Behind the proximal grip, the is handle has its ribbing 56 for a substantial portion of its length and then the distal grip 12b. The chamber 12d passes through the proximal grip, the ribbing, and the distal grip. Opposite the nose, the handle has the button 57 that rotates upon the handle and has its socket to admit a supply line.

Figure 14:
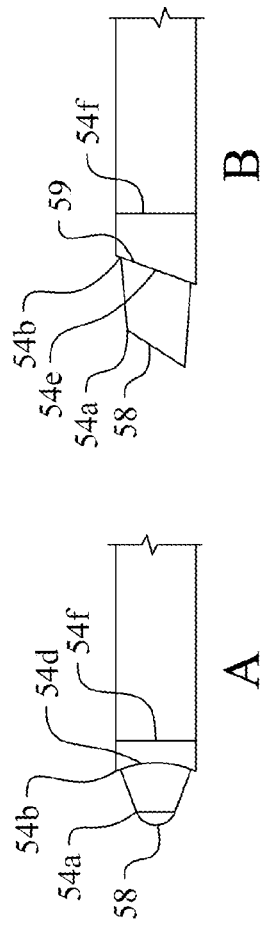
FIG. 14 shows a detailed view of the tube of the instrument.

And, FIG. 14 shows the forward tube in more detailed views. FIG. 14a shows the tube 54 from the top as a surgeon would view it. The forward tube has its narrow width 54a to the left upon the beveled end as at 58. The forward tube expands rearwardly to its maximum width as at 54b. At the maximum width, the second bevel 54d denotes the step in thickness for the remainder of the tube. The beveled end and second bevel have arcs of a concave appearance denoting the direction of the bevel, here in a plane rotated towards the handle but opposite the tab. Rearward of the second bevel, the forward tube has its stepped thickness as shown. Rotating the tube ninety degrees upwardly in the figure to FIG. 14b, the forward tube has its beveled end 58 shown angled into the tube. The beveled end begins at the narrow width 54a and expands outwardly to the maximum width 54b. The second bevel has its side shown here as in 54e. The second bevel extends around the perimeter of the forward tube. Rearward from the second bevel, the forward tube has its stepped thickness as at 59. Rotating the tube another ninety degrees, 180 degrees total, FIG. 14c shows the bottom view of the forward tube opposite that of FIG. 14a. The forward tube has its narrow width 54a at its beveled end 58. Inwardly from the beveled end, the forward tube has its second bevel 54d. The beveled end and the second bevel have convex arcuate forms denoting the plane of the bevels as previously described. Away from the second bevel, the forward tube has its stepped thickness 59. And rotating the tube a last ninety degrees, 270 degrees in total, FIG. 14d shows the forward tube generally opposite that of FIG. 14b. The narrow width 54a of the tube has its beveled end 58 here shown extending downwardly. At the maximum width 54b, the tube has its second bevel 54e generally parallel to the beveled end. Rearwardly from the second bevel, the forward tube has its stepped thickness as at 59.

While the present invention has been related in terms of the foregoing embodiments, those skilled in the art will recognize that the invention is not limited to the embodiments described. The present invention can be practiced with modification and alteration within the spirit and scope of the appended claims. Thus, the description is to be regarded as illustrative instead of restrictive on the present invention.

From the aforementioned description, a corneal endothelial tissue inserter has been described. The device is uniquely capable of allowing a surgeon to retrieve endothelial tissue from a donor's eye, grasp the tissue gently without folding, place the tissue within a small incision in a recipient's eye, and leave the tissue with the least disruption to the corneal region of the recipient's eye. The inserter provides two bevels that guide the surgeon to an angle of insertion and guide the surgeon to prevent over insertion of the instrument into a recipient's eye. The instrument and its various components may be manufactured from many materials, including but not limited to, polymers, steel, ferrous and non-ferrous metals, their alloys, select polymers, and composites.

Various aspects of the illustrative embodiments have been described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations have been set forth in order to provide a thorough understanding of the illustrative embodiments. However, it will be apparent to one skilled in the art that the present invention may be practiced without the is specific details. In other instances, well-known features are omitted or simplified in order not to obscure the illustrative embodiments.

Various operations have been described as multiple discrete operations, in turn, in a manner that is most helpful in understanding the present invention, however, the order of description should not be construed as to imply that these operations are necessarily order dependent. In particular, these operations need not be performed in the order of presentation.

As such, those skilled in the art will appreciate that the conception, upon which this disclosure is based, may readily be utilized as a basis for the designing of other structures, methods and systems for carrying out the several purposes of the present invention. Heretofore, those skilled in the art have not recognized usage of elliptical cross section tubes, a sliding irrigation channel, a beveled nose, and a rotating end button. Therefore, the claims include such equivalent constructions insofar as they do not depart from the spirit and the scope of the present invention.

We claim:

1. A device for delivering endothelial tissue into an eye, said device comprising:
    an elongated handle, generally cylindrical in shape and having a longitudinal axis, a distal end and an opposite proximal end, a rotating button upon said distal end and a nose upon said proximal end;

said handle having a chamber extending lengthwise coaxial with the longitudinal axis of said handle, said chamber extending through said nose and a forward tube extending axially outwardly from said nose and coaxial with said chamber, said forward tube being hollow, tapered, and generally elliptical in cross section, said forward tube having a shape adapted to minimize disruption to an eye and the endothelial tissue;

an irrigation tube, generally elongated and coaxial with the longitudinal axis, said irrigation tube extending through said forward tube and said chamber and partially into said button, said irrigation tube having a forward end proximate said forward tube and an opposite rearward end proximate said distal end;

a flexible platform joining to said forward end of said irrigation tube, said platform gently curving to follow the cross section of said forward tube without folding, said platform adapted to contact the endothelial tissue;

wherein a user operates said device with said platform extended outwardly from said forward tube to retrieve or to deliver the endothelial tissue and with said platform retracted into said forward tube for transporting the endothelial tissue within said instrument;

said forward tube having a beveled end opposite said nose, said beveled end defining the narrowest width of said forward tube, a second beveled edge rearwardly of said beveled end, said forward tube widening rearwardly from its narrowest width to its maximum width at said second beveled edge, and a third edge rearwardly of said second beveled edge and generally perpendicular to the longitudinal axis;

said beveled end and said second beveled edge being mutually parallel and oriented inwardly towards said device;

wherein said beveled end is adapted for insertion of said forward tube into a precise incision in an eye; and, wherein said second beveled edge is adapted to abut the eyeball surface so that a user retains said device within an optimal insertion distance in an eye.

2. The endothelial tissue delivery device of claim 1 further comprising:

said platform having a thin, flexible, planar shape substantially similar to a spade, a leading edge somewhat perpendicular to the longitudinal axis, two wings mutually spaced apart behind said leading edge, each of said wings having maximum width at an inflection point and a trailing edge extending behind each inflection point, said trailing edges joining to a narrow tang, said tang attaching to said forward end of said irrigation tube;

wherein upon a user retracting said irrigation tube into said device, said trailing edges contact said forward tube and begin curling said wings inwardly, said wings following the interior of said forward tube; and, wherein upon a user fully retracting said irrigation tube, said inflection points nearly mutually contact within said forward tube opposite said tang as said wings curl into the interior of said forward tube and said leading edge aligns with an end of said forward tube.

3. The endothelial tissue delivery device of claim 1 further comprising:

said irrigation tube having a closed hemispherical shape upon said forward end attaching to said platform, an angled cut extending from said forward end rearwardly along said irrigation tube to within said nose when said irrigation tube is extended, said angled cut adapted to release an irrigation fluid, a stem rearwardly of said angled cut, said stem being generally perpendicular to said irrigation tube and opposite said platform and said forward tube, said stem extending outwardly from said handle, said stem receiving a tab, said rearward end extending outwardly from said handle into said button; and, said button having a socket therein opposite said handle, said rearward end terminating within said socket thus adapted to connect to an irrigation supply.

4. The endothelial tissue delivery device of claim 3 further comprising:

said chamber having an inner diameter through said nose and a stepped increase of inner diameter away from said nose toward said button;

a slider, generally cylindrical with a diameter that of the stepped diameter of said chamber, said slider fitting upon said irrigation tube at said stem thus stiffening the joining of said stem to said irrigation tube;

said handle having a groove slightly rearward of said nose accessing said chamber, said stem extending into said groove, wherein a user positioning said stem in said groove proximate said nose extends said platform outwardly from said forward tube; and, wherein a user positioning said stem in said groove away from said nose retracts said platform into said forward tube, said groove establishing the maximum extension and retraction of said platform.

5. The endothelial tissue delivery device of claim 1 further comprising:

said handle having a proximal grip rearwardly of said nose and a distal grip inwardly from said button, said proximal grip and said distal grip being generally concave and extending around the circumference of said handle.

6. The endothelial tissue delivery device of claim 5 further comprising:

said distal grip being longer than said proximal grip; and,
said handle including a plurality of ribs between said proximal grip and said distal grip.

7. A device for delivering endothelial tissue into an eye, said device comprising:

an elongated handle, generally cylindrical in shape and having a longitudinal axis, a distal end and an opposite proximal end, a rotating button upon said distal end and a nose upon said proximal end;

said handle having a chamber extending lengthwise coaxial with the longitudinal axis of said handle, said chamber extending through said nose and having an inner diameter through said nose and a stepped increase of inner diameter away from said nose toward said button;

a forward tube extending axially outwardly from said nose and coaxial with said chamber, said forward tube being hollow, tapered, and elliptical in cross section;

an irrigation tube, generally elongated and coaxial with the longitudinal axis, said irrigation tube extending through said forward tube and said chamber and partially into said button chamber, said irrigation tube having a forward end proximate said forward tube outwardly of said nose and an opposite rearward end proximate said distal end, said irrigation tube having a closed hemispherical shape upon said forward end attaching to said platform, an angled cut extending from said forward end rearwardly along said irrigation tube to within said nose when said irrigation tube is extended, said angled cut adapted to release an irrigation fluid, a stem rearwardly of said angled cut, said stem being generally perpendicular to said irrigation tube and opposite said platform and said forward tube, said stem extending outwardly from said handle, said stem receiving a tab, said rearward end extending outwardly from said handle into said button, said button having a socket therein opposite said handle, said rearward end terminating within said socket thus adapted to connect to an irrigation supply;
a flexible platform joining to said forward end of said irrigation tube, said platform gently curving to follow the cross section of said forward tube without folding, said platform adapted to contact the endothelial tissue, said platform having a thin, flexible, planar shape substantially similar to a spade, a leading edge somewhat perpendicular to the longitudinal axis, two wings mutually is spaced apart behind said leading edge, each of said wings having maximum width at an inflection point and a trailing edge extending behind each inflection point, said trailing edges joining to a narrow tang, said tang attaching to said forward end of said irrigation tube;
said forward tube having a shape adapted to minimize disruption to an eye and the endothelial tissue, a beveled end opposite said nose, said beveled end defining the narrowest width of said forward tube, a second beveled edge, said forward tube widening rearwardly from its narrowest width to its maximum width at said second beveled edge, a third edge rearwardly of said second beveled edge and generally perpendicular to the longitudinal axis, said beveled end and said second beveled edge being mutually parallel and oriented inwardly towards said device and away from said platform, wherein said beveled end allows for insertion of said forward tube into a precise incision in an eye, wherein said second beveled edge is adapted to abut the eyeball surface so that a user retains said device within an optimal insertion distance into an eye;
a slider, generally cylindrical with a diameter that of the stepped diameter of said chamber, said slider fitting upon said irrigation tube at said stem thus stiffening the joining of said stem to said irrigation tube;
said handle having a groove slightly rearward of said nose and accessing said chamber, said stem extending into said groove, wherein a user positioning said stem in said groove proximate said nose extends said platform outwardly from said forward tube and a user positioning said stem in said groove away from said nose retracts said platform into said forward tube, said groove establishing the maximum extension and retraction of said platform;
wherein a user operates said device with said platform extended outwardly from said forward tube to retrieve or to deliver the endothelial tissue and with said platform retracted into said forward tube for transporting the endothelial tissue within said instrument;
wherein upon a user retracting said irrigation tube into said device, said trailing edges contact said forward tube and begin curling said wings inwardly, said wings following the interior of said forward tube; and,
wherein upon a user fully retracting said irrigation tube, said inflection points nearly mutually contact within said forward tube opposite said tang as said wings curl into the interior of said forward tube and said leading edge aligns with an end of said forward tube.

8. The endothelial tissue delivery device of claim 7 further comprising:
said handle having a proximal grip rearwardly of said nose and a distal grip inwardly from said button, said proximal grip and said distal grip being generally concave and extending around the circumference of said handle;
said distal grip being longer than said proximal grip; and,
said handle including a plurality of ribs between said proximal grip and said distal grip.

* * * * *